United States Patent [19]
Jørgensen et al.

[11] Patent Number: 6,054,458
[45] Date of Patent: Apr. 25, 2000

[54] HETEROCYCLIC COMPOUNDS

[75] Inventors: Tine Krogh Jørgensen, Ølstykke; Knud Erik Andersen, Smørum; Rolf Hohlweg, Kvistgaard; Uffe Bang Olsen, Vallensbæk; Erik Fischer, Copenhagen S, all of Denmark; Zdenek Polivka, Praha 5; Kaler Sindelar, Praha 4, both of Czech Rep.

[73] Assignee: NovoNordiskals, Bagsvaerd, Denmark

[21] Appl. No.: 09/102,863

[22] Filed: Jun. 23, 1998

Related U.S. Application Data

[60] Provisional application No. 60/052,980, Jul. 7, 1997.

[30] Foreign Application Priority Data

Jun. 25, 1997 [DK] Denmark ................... 0750/97
Apr. 3, 1998 [DK] Denmark ................... 0471/98

[51] Int. Cl.⁷ .............. A61K 31/496; C07D 241/04; C07D 407/04; C07D 409/04
[52] U.S. Cl. .............. 514/255; 540/522; 544/361; 544/364; 544/375; 544/381
[58] Field of Search ............... 544/361, 364, 544/375, 381; 540/522; 514/255

[56] References Cited

U.S. PATENT DOCUMENTS

| | | | |
|---|---|---|---|
| 3,632,572 | 1/1972 | Walker et al. | 540/522 |
| 3,985,750 | 10/1976 | Protiva et al. | 544/359 |
| 4,616,023 | 10/1986 | Remy et al. | 514/404 |

FOREIGN PATENT DOCUMENTS

| | | |
|---|---|---|
| 0 406 739 | 1/1991 | European Pat. Off. |
| 0 451 772 | 10/1991 | European Pat. Off. |
| 0 682 015 | 11/1995 | European Pat. Off. |
| 2 256 392 | 5/1973 | Germany . |
| WO 92/20658 | 11/1992 | WIPO . |

OTHER PUBLICATIONS

Jilek et al. "Tricyclic analogs of the antiallergic agent oxatomide . . . " CA 111:97179, 1988.
Greene "Protective groups in organic synthesis" John Wiley, p. 154–155, 1982.
Burger "A guide to the chemical basis of drug dexign" Wiley interscience p. 15, 1983.
Iwasaki et al., Chem. Pharm. Bull., vol. 42, No. 11, pp. 2285–2290 (Nov. 1994).

*Primary Examiner*—Celia Chang
*Attorney, Agent, or Firm*—Steve T. Zelson; Carol E. Rozek

[57] ABSTRACT

The present invention relates to novel N-substituted azaheterocyclic compounds of the general formula

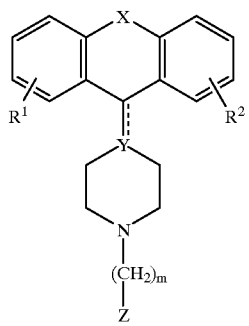

wherein X, Y, Z, $R^1$, $R^2$ and m are as defined in the detailed part of the present description, or salts thereof, to methods for their preparation, to compositions containing them, and to their use for the clinical treatment of painful, hyperalgesic and/or inflammatory conditions in which C-fibers play a pathophysiological role by eliciting neurogenic pain or inflammation, as well as their use for treatment of indications caused by or related to the secretion and circulation of insulin antagonising peptides, e.g. non-insulin-dependent diabetes mellitus (NIDDM) and ageing-associated obesity.

18 Claims, No Drawings

HETEROCYCLIC COMPOUNDS

CROSS-REFERENCE TO RELATED APPLICATIONS

This application claims priority under 35 U.S.C. 119 of Danish application nos. 0750/97 filed Jun. 25, 1997 and 0471/98 filed Apr. 3, 1998, and U.S. provisional application Ser. No. 60/052,980 filed Jul. 7, 1997, the contents of which are fully incorporated herein by reference.

FIELD OF INVENTION

The present invention relates to novel N-substituted azaheterocyclic compounds in which a substituted alkyl chain forms part of the N-substituent or salts thereof, to methods for their preparation, to compositions containing them, to the use of the compounds for preparing compositions for the clinical treatment of painful, hyperalgesic and/or inflammatory conditions in which C-fibres play a pathophysiological role by eliciting neurogenic pain or inflammation, and to methods of treating said painful, hyperalgesic and/or inflammatory conditions. The invention also relates to the use of the present compounds for the treatment of insulin resistance in non-insulin-dependent diabetes mellitus (NIDDM) as well as ageing-associated obesity, the present compounds being known to interfere with neuropeptide containing C-fibres and hence to inhibit the secretion and circulation of insulin antagonising peptides like CGRP or amylin.

BACKGROUND OF INVENTION

The nervous system exerts a profound effect on the inflammatory response. Antidromic stimulation of sensory nerves results in localised vasodilation and increased vascular permeability (Janecso et al. Br. J. Pharmacol. 1967, 31, 138–151), and a similar response is observed following injection of peptides known to be present in sensory nerves. From this and other data it is postulated that peptides released from sensory nerve endings mediate many inflammatory responses in tissues like skin, joint, urinary tract, eye, meninges, gastro-intestinal and respiratory tracts. Hence inhibition of sensory nerve peptide release and/or activity may be useful in treatment of for example arthritis, dermatitis, rhinitis, asthma, cystitis, gingivitis, thrombophlelitis, glaucoma, gastro-intestinal diseases or migraine.

Further, the potent effects of CGRP on skeletal muscle glycogen synthase activity and muscle glucose metabolism, together with the notion that this peptide is released from the neuromuscular junction by nerve excitation, suggest that CGRP may play a physiological role in skeletal muscle glucose metabolism by directing the phosphorylated glucose away from glycogen storage and into the glycolytic and oxidative pathways (Rossetti et al. Am. J. Physiol. 264, E1–E10, 1993). This peptide may represent an important physiological modulator of intracellular glucose trafficking in physiological conditions, such as exercise, and may also contribute to the decreased insulin action and skeletal muscle glycogen synthase in pathophysiological conditions like NIDDM or ageing-associated obesity (Melnyk et al. Obesity Res. 3, 337–344, 1995) where circulating plasma levels of CGRP are markedly increased. Hence inhibition of release and/or activity of the neuropeptide CGRP may be useful in the treatment of insulin resistance related to type 2 diabetes or ageing.

In U.S. Pat. No. 4,383,999 and U.S. Pat. No. 4,514,414 and in EP 236342 as well as in EP 231996 some derivatives of N-(4,4-disubstituted-3-butenyl)azaheterocyclic carboxylic acids are claimed as inhibitors of GABA uptake. In EP 342635 and EP 374801, N-substituted azaheterocyclic carboxylic acids in which an oxime ether group and vinyl ether group forms part of the N-substituent respectively are claimed as inhibitors of GABA uptake. Further, in WO 9107389 and WO 9220658, N-substituted azacyclic carboxylic acids are claimed as GABA uptake inhibitors. EP 221572 claims that 1-aryloxyalkylpyridine-3-carboxylic acids are inhibitors of GABA uptake.

EP 451772 and EP 406739 as well as Chem. Pharm. Bull. 42, 2285 (1994) discloses (dibenzo[a,d]cyclohepten-5-ylidene)piperidine derivatives and related compounds which have antihistaminergic and antiallergic activity.

SUMMARY OF THE INVENTION

The present invention relates to compounds of the general formulae I and Ia, wherein X, Y, Z, $R^1$, $R^2$, $R^3$ and m are as defined in the detailed part of the present description.

The present compounds are useful for the treatment, prevention, elimination, alleviation or amelioration of an indication related to all painful, hyperalgesic and/or inflammatory conditions in which C-fibres play a pathophysiological role, e.g. neurogenic pain, neurogenic inflammation, migraine, neuropathy, itching and rheumatoid arthritis, as well as indications caused by or related to the secretion and circulation of insulin antagonising peptides and other peptides derived from the sensory nervous system, e.g. non-insulin-dependent diabetes mellitus (NIDDM) and ageing-associated obesity.

In another aspect, the present invention includes within its scope pharmaceutical compositions comprising, as an active ingredient, at least one of the compounds of the general formulae or a pharmaceutically acceptable salt thereof together with a pharmaceutically acceptable carrier or diluent.

In another aspect of the present invention there is provided a method of treating painful, hyperalgesic and/or inflammatory conditions in which C-fibres play a pathophysiological role, e.g. neurogenic pain, neurogenic inflammation, migraine, neuropathy, itching and rheumatoid arthritis, as well as a method of treating indications caused by or related to the secretion and circulation of insulin antagonising peptides, e.g. non-insulin-dependent diabetes mellitus (NIDDM) and ageing-associated obesity.

The method of treatment may be described as the treatment, prevention, elimination, alleviation or amelioration of one of the above indications, which comprises the step of administering to the said subject a neurologically effective amount of a compound of the invention, or a pharmaceutically acceptable salt thereof.

A further aspect of the invention relates to the use of a compound of the present invention for the preparation of a pharmaceutical composition for the treatment of all painful, hyperalgesic and/or inflammatory conditions in which C-fibres play a pathophysiological role, e.g. neurogenic pain, neurogenic inflammation, migraine, neuropathy, itching and rheumatoid arthritis, as well as for the treatment of indications caused by or related to the secretion and circulation of insulin antagonising peptides, e.g. non-insulin-dependent diabetes mellitus (NIDDM) and ageing-associated obesity.

Further objects will become apparent from the following description.

DETAILED DESCRIPTION OF THE INVENTION

Accordingly, the present invention relates to novel N-substituted azaheterocyclic compounds of the general formula I

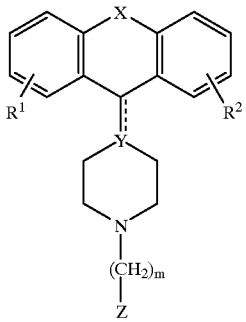

(I)

wherein $R^1$ and $R^2$ independently are hydrogen, halogen, trifluoromethyl, hydroxy, $C_{1-4}$-alkyl or $C_{1-6}$-alkoxy;

X is ortho-phenylene, —O—, —S—, —C($R^6R^7$)—, —$CH_2CH_2$—, —CH=CH—$CH_2$—, —$CH_2$—CH=CH—, —$CH_2$—(C=O)—, —(C=O)—$CH_2$—, —$CH_2CH_2CH_2$—, —CH=CH—, —N($R^8$)—(C=O)—, —(C=O)—N($R^8$)—, —O—$CH_2$—, —$CH_2$—O—, —$OCH_2$O—, —S—$CH_2$—, —$CH_2$—S—, —($CH_2$)N($R^8$)—, —N($R^8$)($CH_2$)—, —N($CH_3$)$SO_2$—, —$SO_2$N($CH_3$)—, —CH($R^{10}$)$CH_2$—, —$CH_2$CH($R^{10}$)—, —(C=O)—, —N($R^9$)— or —(S=O)— wherein $R^6$, $R^7$, $R^8$ and $R^9$ independently are hydrogen or $C_{1-6}$-alkyl, and wherein $R^{10}$ is $C_{1-6}$-alkyl or phenyl;

Y is C or N; ⸺ is optionally a single bond or a double bond, and ⸺ is a single bond when Y is N;

m is 1, 2, 3, 4, 5 or 6; and

Z is —$COOR^3$ or

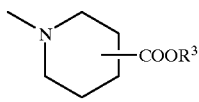

wherein $R^3$ is H or $C_{1-6}$-alkyl;

or a pharmaceutically acceptable salt thereof.

The present invention also relates to the novel N-substituted azaheterocyclic compounds of the general formula Ia

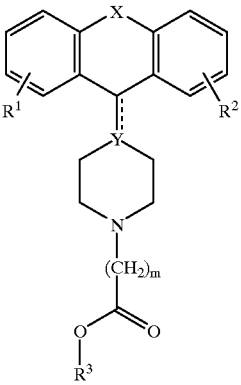

(Ia)

wherein $R^1$ and $R^2$ independently are hydrogen, halogen, trifluoromethyl, hydroxy, $C_{1-6}$-alkyl or $C_{1-6}$-alkoxy;

X is ortho-phenylene, —O—, —S—, —C($R^6R^7$)—, —$CH_2CH_2$—, —CH=CH—$CH_2$—, —$CH_2$—CH=CH—, —$CH_2$—(C=O)—, —(C=O)—$CH_2$—, —$CH_2CH_2CH_2$—, —CH=CH—, —N($R^8$)—(C=O)—, —(C=O)—N($R^8$)—, —O—$CH_2$—, —$CH_2$—O—, —$OCH_2$O—, —S—$CH_2$—, —$CH_2$—S—, —($CH_2$)N($R^8$)—, —N($R^8$)($CH_2$)—, —N($CH_3$)$SO_2$—, —$SO_2$N($CH_3$)—, —CH($R^{10}$)$CH_2$—, —$CH_2$CH($R^{10}$)—, —(C=O)—, —N($R^9$)— or —(S=O)— wherein $R^6$, $R^7$, $R^8$ and $R^9$ independently are hydrogen or $C_{1-6}$-alkyl, and wherein $R^{10}$ is $C_{1-6}$-alkyl or phenyl;

Y is C or N;

⸺ is optionally a single bond or a double bond, and ⸺ is a single bond when Y is N;

m is 1, 2, 3, 4, 5 or 6; and $R^3$ is H or $C_{1-6}$-alkyl;

or a pharmaceutically acceptable salt thereof.

Compounds of the general formulae wherein $R^1$ and $R^2$ are hydrogen; X is —O—, —S—, —$CH_2CH_2$—, —CH=CH—, —O—$CH_2$—, —$CH_2$—O—, —S—$CH_2$— or —$CH_2$—S—; Y is C and ⸺ is a double bond; m is 1, 2, 3, 4, 5 or 6; Z is —$COOR^3$ and $R^3$ is H or $C_{1-6}$-alkyl are known from EP A 451772 and EP A 406739 as well as Chem. Pharm. Bull. 42, 2285 (1994) as compounds having antihistaminergic and antiallergic activity.

The compounds according to the invention may exist as geometric and optical isomers and all isomers, as separated, pure or partially purified stereoisomers or racemic mixtures thereof are included in the scope of the invention. Isomers may be separated by means of standard methods such as chromatographic techniques or fractional crystallisation of suitable salts. Preferably, the compounds according to the invention exist as the individual geometric or optical isomers.

The compounds according to the invention may optionally exist as pharmaceutically acceptable acid addition salts, metal salts or, optionally alkylated, ammonium salts.

Examples of such salts include inorganic and organic acid addition salts such as hydrochloride, hydrobromide, sulphate, phosphate, acetate, fumarate, maleate, citrate, lactate, tartrate, oxalate or similar pharmaceutically acceptable inorganic or organic acid addition salts. Further examples of pharmaceutically acceptable inorganic or organic acid addition salts include the pharmaceutically acceptable salts listed in *Journal of Pharmaceutical Science*, 66, 2 (1977) which are known to the skilled artisan.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds according to the invention may be administered in a pharmaceutically acceptable acid addition salt form or where possible as a metal or a lower alkylammonium salt. Such salt forms exhibit approximately the same order of activity as the free base forms.

In the above structural formulae and throughout the present specification, the following terms have the indicated meaning:

The term "$C_{1-6}$-alkyl" as used herein, alone or in combination, refers to a straight or branched, saturated hydrocarbon chain having 1 to 6 carbon atoms. Typical $C_{1-6}$-alkyl groups include, but are not limited to, methyl, ethyl, n-propyl, iso-propyl, n-butyl, sec-butyl, iso-butyl, tert-butyl, n-pentyl, iso-pentyl, 2-methylbutyl, 3-methylbutyl, n-hexyl, iso-hexyl, 4-methylpentyl, neopentyl, 1,2-dimethylpropyl, 2,2-dimethylpropyl, 1,2,2-trimethylpropyl and the like.

The term "$C_{1-6}$-alkoxy" as used herein, alone or in combination is intended to include those $C_{1-6}$-alkyl groups of the designated length in either a linear or branched or cyclic configuration linked through an ether oxygen having its free valence bond from the ether oxygen. Examples of linear alkoxy groups are methoxy, ethoxy, propoxy, butoxy, pentoxy and hexoxy. Examples of branched alkoxy are isopropoxy, sec-butoxy, tert-butoxy, isopentoxy and isohexoxy. Example of cyclic alkoxy are cyclopropyloxy, cyclobutyloxy, cyclopentyloxy and cyclohexyloxy.

The term "halogen" means fluorine, chlorine, bromine or iodine.

In a preferred embodiment of the invention $R^1$ and $R^2$ are selected from hydrogen, halogen, trifluoromethyl or $C_{1-6}$-alkyl. Preferably $R^1$ and $R^2$ are hydrogen.

In another preferred embodiment of the invention Y is N.

In another preferred embodiment of the invention Y is C and ⸺ is a double bond.

In another preferred embodiment of the invention X is selected from —S—, —CH$_2$CH$_2$—, —CH═CH—, —O—CH$_2$—, —CH$_2$—O—, —S—CH$_2$— or —CH$_2$—S—. Preferably X is —CH$_2$CH$_2$—.

In another preferred embodiment of the invention X is —S—CH$_2$— or —CH$_2$—S—.

In another preferred embodiment of the invention m is 1, 2, 3 or 4.

In another preferred embodiment of the invention Z is —COOR$^3$.

In another preferred embodiment of the invention Z is

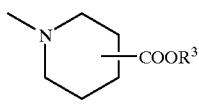

In yet another preferred embodiment of the invention $R^3$ is H.

Preferred compounds of the present invention include:
2-(4-(10,11-Dihydro-5H-dibenzo[a,d]cyclohepten-5-yl) piperazin-1-yl)acetic acid,
3-(4-(10,11-Dihydro-5H-dibenzo[a,d]cyclohepten-5-yl) piperazin-1-yl)propionic acid,
4-(4-(10,11-Dihydro-5H-dibenzo[a,d]cyclohepten-5-yl) piperazin-1-yl)butyric acid,
5-(4-(10,11-Dihydro-5H-dibenzo[a,d]cyclohepten-5-yl) piperazin-1-yl)pentanoic acid,
or a pharmaceutically acceptable salt thereof.

Other preferred compounds of the present invention include:
1-(3-(4-(6,11-Dihydrodibenzo[b,e]thiepin-11-ylidene)-1-piperidinyl)-1-propyl)-3-piperidinecarboxylic acid,
(R)-1-(2-(4-(6,11-Dihydrodibenzo[b,e]thiepin-11-ylidene) piperidin-1-yl)ethyl)-3-piperidinecarboxylic acid,
or a pharmaceutically acceptable salt thereof.

It has been demonstrated that the compounds according to the invention inhibit neurogenic inflammation which involves the release of neuropeptides from peripheral and central endings of sensory C-fibres. Experimentally this can be demonstrated in animal models of histamine induced paw oedema Amann et al. (Europ. J. Pharmacol. 279, 227–231, 1995) in which the compounds according to the invention exhibit a potent inhibitory effect. The compounds according to the invention may be used to treat all painful, hyperalgesic and/or inflammatory conditions in which C-fibres play a pathophysiological role by eliciting neurogenic pain or inflammation, i.e.:

Acutely painful conditions exemplified by migraine, post-operative pain, burns, bruises, post-herpetic pain (Zoster) and pain as it is generally associated with acute inflammation; chronic, painful and/or inflammatory conditions exemplified by various types of neuropathy (diabetic, post-traumatic, toxic), neuralgia, rheumatoid arthritis, spondylitis, gout, inflammatory bowel disease, prostatitis, cancer pain, chronic headache, coughing, asthma, itching, chronic pancreatitis, inflammatory skin disease including psoriasis and autoimmune dermatoses, osteoporotic pain.

Also included within the present invention are the use of the compounds of the general formula I

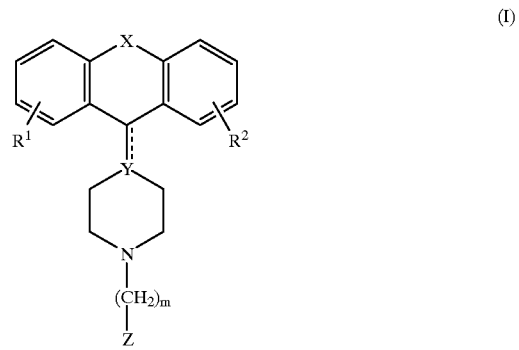

(I)

wherein $R^1$ and $R^2$ are hydrogen;
X is —O—, —S—, —CH$_2$CH$_2$—, —CH═CH—, —O—CH$_2$—, —CH$_2$—O—, —S—CH$_2$— or —CH$_2$—S—;
Y is C and ⸺ is a double bond;
m is 1, 2, 3, 4, 5 or 6;
Z is —COOR$^3$ and $R^3$ is H or $C_{1-6}$-alkyl,
or a pharmaceutically acceptable salt thereof, for the preparation of pharmaceutical compositions for the treatment of neurogenic inflammation, painful and/or inflammatory conditions e.g. neuropathy and rheumatoid arthritis.

Further, it has been demonstrated that the compounds according to the invention improves the glucose tolerance in diabetic ob/ob mice and that this may result from the reduced release of CGRP from peripheral nervous endings. Hence the compounds according to the invention may be used in the treatment of NIDDM as well as ageing-associated obesity. Experimentally this has been demonstrated by the subcutaneous administration of glucose into ob/ob mice with or without previous oral treatment with a compound according to the invention.

Also included within the present invention are the use of the compounds of the general formula I

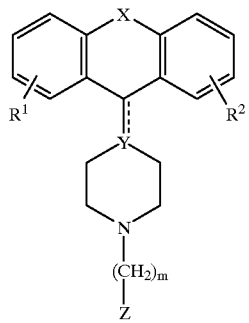

(I)

wherein $R^1$ and $R^2$ are hydrogen;
X is —O—, —S—, —CH$_2$CH$_2$—, —CH=CH—, —O—CH$_2$—, —CH$_2$—O—, —S—CH$_2$— or —CH$_2$—S—;
Y is C and ⁓ is a double bond;
m is 1, 2, 3, 4, 5 or 6;
Z is —COOR$^3$ and $R^3$ is H or C$_{1-6}$-alkyl,
or a pharmaceutically acceptable salt therof, for the preparation of pharmaceutical compositions for reducing blood glucose. Hence these compounds may be used in the treatment non-insulin-dependent diabetes mellitus (NIDDM), as well as in the treatment of insulin resistance in NIDDM.

The compounds of the general formula I, wherein Y is N, may be prepared by the following methods:

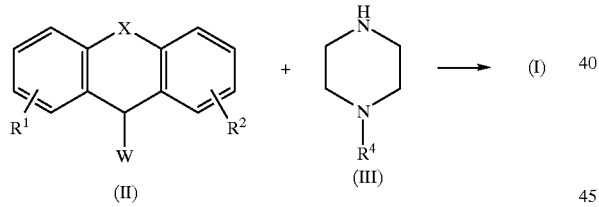

A compound of formula II wherein $R^1$, $R^2$ and X are as defined above and W is a suitable leaving group such as halogen, p-toluene sulphonate or mesylate may be reacted with a piperazine of formula III wherein $R^4$ is hydrogen, a suitable N-protecting group, —(CH$_2$)$_m$—CO$_2$R$^3$ or

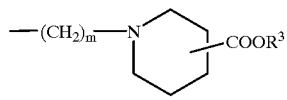

wherein $R^3$ is as defined above. Introduction and removal of such groups is described in "Protective Groups in Organic Chemistry" J. F. W. McOrnie ed. (New York, 1973).

This alkylation reaction may be carried out in a solvent such as acetone, dibutylether, 2-butanone, dioxane, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h.

When $R^4$ in formula III is hydrogen, a second N-alkylation with a compound Hal(CH$_2$)$_m$—CO$_2$R$^3$ or

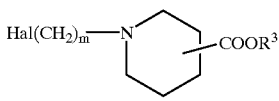

follows, where Hal means a halogen and $R^3$ and m are as defined above.

When $R^4$ in formula III is a protecting group then, after deprotection, a second N-alkylation with a compound Hal (CH$_2$)$_m$—CO$_2$R$^3$ or

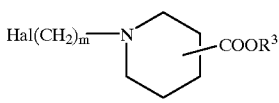

follows. When $R^3$ is an C$_{1-6}$-alkyl group, a final deprotection step may be performed.

The compounds of the general formula I, wherein Y is C, may be prepared by the following methods:

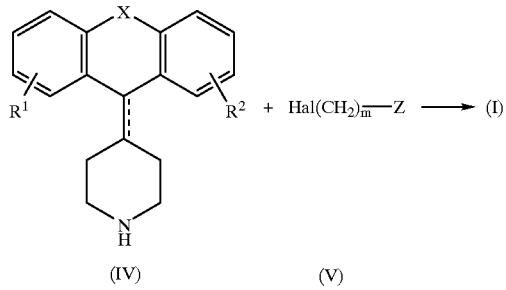

A compound of formula IV wherein $R^1$, $R^2$ and X are as defined may be reacted with a compound of formula V, where Hal means a halogen, Z means —COOR$^3$ or

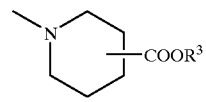

and $R^3$ and m are as defined above. This alkylation reaction may be carried out in a solvent such as acetone, dibutylether, 2-butanone, dioxane, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h.

When $R^3$ is an C$_{1-6}$-alkyl group, a final deprotection step may be performed.

The compounds of formula Ia, wherein Y is N, may be prepared by the following methods:

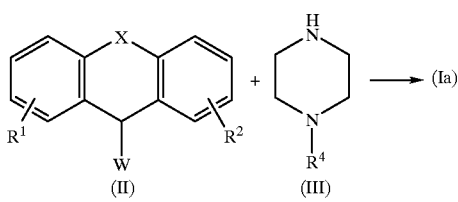

A compound of formula II wherein $R^1$, $R^2$ and X are as defined above and W is a suitable leaving group such as halogen, p-toluene sulphonate or mesylate may be reacted with a piperazine of formula III wherein $R^4$ is hydrogen, a suitable N-protecting group or $-(CH_2)_m-CO_2R^3$ wherein $R^3$ is as defined above. Introduction and removal of such groups is described in "Protective Groups in Organic Chemistry" J. F. W. McOrnie ed. (New York, 1973).

This alkylation reaction may be carried out in a solvent such as acetone, dibutylether, 2-butanone, dioxane, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h.

When $R^4$ in formula III is hydrogen, a second N-alkylation with a compound $Hal(CH_2)_m-CO_2R^3$ follows, where Hal means a halogen and $R^3$ and m are as defined above.

When $R^4$ in formula III is a protecting group then, after deprotection, a second N-alkylation with a compound $Hal(CH_2)_m-CO_2R^3$ follows. When $R^3$ is an $C_{1-6}$-alkyl group, a final deprotection step may be performed.

Compounds of formula Ia, wherein Y is C, may be prepared by the following methods:

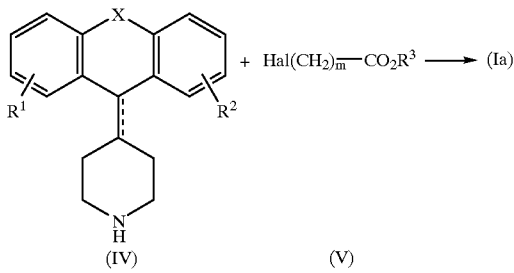

A compound of formula IV wherein $R^1$, $R^2$ and X are as defined may be reacted with a compound of formula V, where Hal means a halogen and $R^3$ and m are as defined above. This alkylation reaction may be carried out in a solvent such as acetone, dibutylether, 2-butanone, dioxane, ethyl acetate, tetrahydrofuran (THF) or toluene in the presence of a base e.g. sodium hydride or potassium carbonate and a catalyst, e.g. an alkali metal iodide at a temperature up to reflux temperature for the solvent used for e.g. 1 to 120 h.

When $R^3$ is an $C_{1-6}$-alkyl group, a final deprotection step may be performed.

Compounds of formula IV and V may readily be prepared by methods familiar to those skilled in the art.

Pharmacological Methods

I. Histamine induced paw oedema

The rat histamine paw oedema test was performed essentially as described by Amann et al. (Europ. J. Pharmacol. 279, 227–231, 1995). In brief 250–300 g male Sprague-Dawley rats were anaesthetized with pentobarbital sodium, and placed on a 32 degree heated table. Ten minutes later histamine (50 micoliter, 3 mg/ml) was injected in the right hind paw and 20 minutes hereafter the paw swelling was determined by water plethysmography (Ugo Basile). Test compounds were administered intraperitoneally at 15 minutes before the anaesthetics.

II. Histamine induced hyperglycemia in mice

Conscious unfasted 25 g male NMRI mice are administered histamine chloride (90 nmol) icv according to the method of Nishibori et al. (J. Pharmacol. Exp. Therap. 241, 582–286, 1987). Blood glucose is determined at time 0 and 40 min after the histamine injection. Test compounds are administered at 1.0 mg/kg ip 30 min before the histamine injection, and % inhibition refers to the capacity of the compounds to inhibit the histamine induced blood glucose rise.

III. Reduced release of CGRP ob/ob female mice, 16 weeks of age, where injected glucose (2g/kg) subcutaneously. At times hereafter blood glucose was determined in tail venous blood by the glucose oxidase method. At the end of the study the animals were decapitated and trunck blood collected. Immunoreactive CGRP was determined in plasma by radio-immuno-assay. Two groups of animals were used. The one group was vehicle treated, whereas the other group received a compound of formula I via drinking water (100 mg/l) for five days before the test.

Values for inhibition of histamine induced oedema response for a representative compound is listed in table I.

TABLE I

Inhibition of histamine induced paw oedema at 1.0 mg/kg

| Example no. | % inhibition |
| --- | --- |
| 2 | 44 |
| 10 | 33 |

Values for inhibition of histamine induced hyperglycemia for a representative compound is listed in table II.

TABLE II

Inhibition of histamine induced hyperglycemia at 1.0 mg/kg

| Example no. | % inhibition |
| --- | --- |
| 10 | 69 |

Pharmaceutical compositions

The present invention also relates to pharmaceutical compositions comprising, as an active ingredient, at least one of the compounds of the invnetion or a pharmaceutically acceptable salt thereof and, usually, such compositions also contain a pharmaceutically acceptable carrier or diluent.

Pharmaceutical compositions comprising a compound of the present invention may be prepared by conventional techniques, e.g. as described in *Remington: The Science and Practise of Pharmacy.* $19^{th}$ Ed., 1995. The compositions may appear in conventional forms, for example capsules, tablets, aerosols, solutions, suspensions or topical applications.

Typical compositions include a compound of the invention or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, syrup, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, topical, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
|---|---|
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9–40 T approx. | 0.9 mg |

*Acylated monoglyceride used as plasticizer for film coating.

The compounds of the invention may be administered to a mammal, especially a human in need of such treatment, prevention, elimination, alleviation or amelioration of an indication related to all painful, hyperalgesic and/or inflammatory conditions in which C-fibres play a pathophysiological role such as e.g. neurogenic pain, neurogenic inflammation, migraine, neuropathy, itching and rheumatoid arthritis, as well as indications caused by or related to the secretion and circulation of insulin antagonising peptides, such as non-insulin-dependent diabetes mellitus (NIDDM) or ageing-associated obesity. Such mammals include also animals, both domestic animals, e.g. household pets, and non-domestic animals such as wildlife.

The compounds of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, in an effective amount.

The compounds of the invention are effective over a wide dosage range. For example, in the treatment of humans, dosages from about 0.5 to about 1000 mg, preferably from about 1 to about 500 mg of compounds of the present invention, conveniently given from 1 to 5 times daily. A most preferable dosage is from about 50 to about 200 mg per dose when administered to e.g. a human. The exact dosage will depend upon the mode of administration, on the therapy desired, form in which administered, the subject to be treated and the body weight of the subject to be treated, and the preference and experience of the physician or veterinarian in charge.

Generally, the compounds of the present invention are dispensed in unit dosage form comprising from about 50 to about 200 mg of active ingredient in or together with a pharmaceutically acceptable carrier per unit dosage.

Usually, dosage forms suitable for oral, nasal, pulmonal or transdermal administration comprise from about 0.5 mg to about 1000 mg, preferably from about 1 mg to about 500 mg of the compounds of formula I admixed with a pharmaceutically acceptable carrier or diluent.

The method of treating may be described as the treatment of an indication caused by or related to the secretion and circulation of insulin antagonising peptides like CGRP or amylin in a subject in need thereof, which comprises the step of administering to the said subject a neurologically effective amount of a compound of the invention, or a pharmaceutically acceptable salt thereof.

Any novel feature or combination of features described herein is considered essential to this invention.

EXAMPLES

The process for preparing compounds of the present invention and preparations containing them is further illustrated in the following examples, which, however, are not to be construed as limiting.

Hereinafter, TLC is thin layer chromatography, CDCl₃ is deuterio chloroform and DMSO-d₆ is hexadeuterio dimethylsulfoxide. The structures of the compounds are confirmed by either elemental analysis or NMR, where peaks assigned to characteristic protons in the title compounds are presented where appropriate. ¹H NMR shifts ($\delta_H$) are given in parts per million (ppm). M.p. is melting point and is given in ° C. and is not corrected. Column chromatography was carried out using the technique described by W. C. Still et al, J. Org. Chem. (1978), 43, 2923–2925 on Merck silica gel 60 (Art. 9385). Compounds used as starting materials are either known compounds or compounds which can readily be prepared by methods known per se.

Example 1
2-(4-(10,11-Dihydro-5H-dibenzo[a,d]cyclohepten-5-yl)piperazin-1-yl)acetic acid

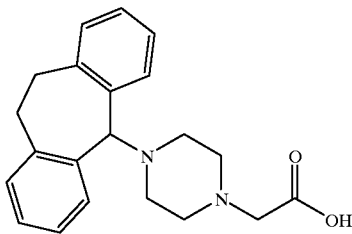

5-Chlorodibenzosuberane (10.0 g, 43 mmol) and piperazine (18.0 g, 218 mmol) was suspended in 1,4-dioxane (300 ml) and heated at reflux temperature for 6 h. The reaction mixture was cooled to room temperature and filtered. To the filtrate water (300 ml) was added, pH was adjusted to 10 with saturated sodium hydrogen carbonate and the mixture was extracted with dichloromethane (3×75 ml). The combined organic extracts were washed with water (150 ml), dried (MgSO₄) and concentrated in vacuo. Dichloromethane (50 ml) was added, and the solution was filtered. The filtrate was subjected to column chromatography on silica gel (130 g) by first eluting with dichloromethane (150 ml) and then dichloromethane/methanol=9:1 (250 ml). This furnished 4.5 g of crude product which was recrystallised from heptane affording 4.2 g (33%) of 1-(10,11-dihydro-5H-dibenzo[a,d]cyclohepten-5-yl)piperazine.

¹H-NMR (300 MHz, CDCl₃) δ 7.10 (m, 8H), 4.00 (m, 2H), 3.95 (s, 1H), 2.75 (m, 6H), 2.25 (s, 4H).

The piperazine from the step above (1.0 g, 3.6 mmol), ethyl 2-chloroacetate (0.5 g, 4.0 mmol), and potassium carbonate (0.5 g, 4 mmol) were suspended in acetonitrile (50 ml) and allowed to react at 50° C. for 4 h. The crude reaction mixture was subjected to column chromatography on silica gel (30 g) by first eluting with dichloromethane (50 ml) and then dichloromethane/methanol=9:1 (250 ml). This furnished 1.05 g (73%) of 2-(4-(10,₁1-dihydro-5H-dibenzo[a,d]cyclohepten-5-yl)piperazin-1-yl)acetic acid ethyl ester.

¹H-NMR (300 MHz, CDCl₃) δ 7.0 (m, 8H), 4.13 (q, 2H), 2.95 (m, 3H), 3.10 (s, 2H), 2.74 (m, 2H), 2.40 (d, 8H), 1.20 (t, 3H).

The ester from the above step (1.05 g, 2.9 mmol), sodium hydroxide (0.8 g, 20 mmol) and water (2 ml) was dissolved in ethanol (50 ml) and allowed to react at 50° C. for 2 h. After cooling to room temperature, water (150 ml) was added and the reaction mixture was adjusted to pH 2 with 1 N hydrochloric acid and extracted with dichloromethane (3×50 ml). The combined organic extracts were dried (MgSO₄) and concentrated in vacuo. The resulting oil was stripped with acetone (2×20 ml), dissolved in dichloromethane (20 ml) and precipitated with petroleum ether. The resulting solid was dried under vacuum for 24 h leaving the title compound (0.56 g, 57%).

HPLC retention time=17.55 minutes (5 μm C18 4×250 mm column, eluting with a 20–80% gradient of 0.1% trifluoroacetic acid/acetonitrile and 0.1% trifluoroacetic acid/water over 30 minutes at room temperature).

¹H-NMR (300 MHz, CDCl₃) δ 7.10 (m, 8H), 4.12 (s, 1H), 3.87 (m, 2H), 3.63 (s, 2H), 3.22 (bs, 4H), 2.80 (m, 2H), 2.65 (s, 4H).

Example 2

3-(4-(10,11-Dihydro-5H-dibenzo[a,d]cyclohepten-5-yl)piperazin-1-yl)propionic acid hydrochloride

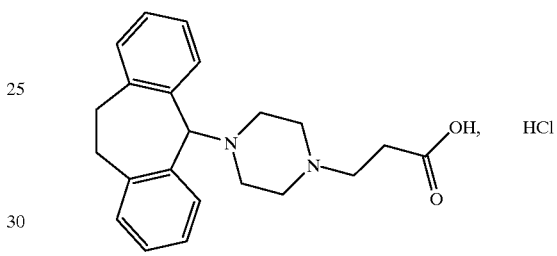

1-(10,11-Dihydro-5H-dibenzo[a,d]cyclohepten-5-yl)piperazine (prepared as described in Example 1, 1.0 g, 3.6 mmol), ethyl 3-bromopropionate (0.71 g, 3.9 mmol), and potassium carbonate (0.5 g, 4 mmol) were suspended in acetonitrile (50 ml) and allowed to react at 50° C. for 4 h. The crude reaction mixture was subjected to column chromatography on silica gel (30 g) by first eluting with dichloromethane (50 ml) and then dichloromethane/methanol=9:1 (250 ml). This furnished 1.15 g (84%) of 3-(4-(10,11-dihydro-5H-dibenzo[a,d]cyclohepten-5-yl)piperazin-1-yl) propionic acid ethyl ester.

¹H-NMR (300 MHz, CDCl₃) δ 7.10 (m, 8H), 4.13 (q, 2H), 2.95 (m, 3H), 2.77 (m, 2H), 2.62 (t, 2H), 2.41 (t, 2H), 2.30 (bd, 8H) 1.20 (t, 3H).

The ester from the above step (1.15 g, 3.0 mmol), sodium hydroxide (0.8 g, 20 mmol) and water (2 ml) were dissolved in ethanol (50 ml) and allowed to react at 50° C. for 2 h. After cooling to room temperature, water (150 ml) was added, and the reaction mixture was adjusted to pH 2 with 1 N hydrochloric acid and extracted with dichloromethane (3×50 ml). The combined organic extracts were dried (MgSO₄) and concentrated in vacuo. The resulting oil was stripped with acetone (2×20 ml), reprecipitated from acetone and dried under vacuum for 24 h leaving the title compound (0.80 g, 69%) as an amorphous solid.

Calculated for C₂₂H₂₆N₂O₂, HCl: C, 68.55%; H, 7.05%; N, 7.27%; Found: C, 68.29%; H, 7.03%; N, 7.24%.

¹H-NMR (300 MHz, CDCl₃) δ 7.10 (m, 8H), 4.17 (s, 1H), 3.88 (m, 2H), 3.50–3.10 (bs, 2H), 3.29 (t, 2H), 2.93 (t, 2H), 2.80 (m, 2H), 2.72 (s, 6H).

Example 3
4-(4-(10,11-Dihydro-5H-dibenzo[a,d]cyclohepten-5-yl)piperazin-1-yl)butyric acid hydrochloride

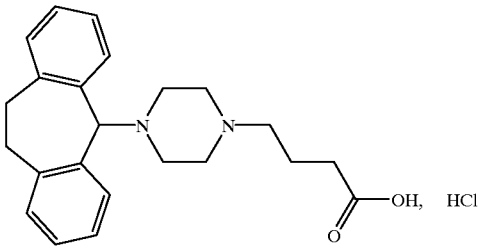

1-(10,11-Dihydro-5H-dibenzo[a,d]cyclohepten-5-yl)piperazine (prepared as described in Example 1, 1.0 g, 3.6 mmol), ethyl 4-bromobutyrate (0.76 g, 3.9 mmol), and potassium carbonate (0.5 g, 4 mmol) were suspended in acetonitrile (50 ml) and allowed to react at 50° C. for 3 h. The crude reaction mixture was subjected to column chromatography on silica gel (30 g) by first eluting with dichloromethane (50 ml) and then dichloromethane/methanol=9:1 (250 ml). This furnished 1.2 g (85%) of 4-(4-(10,11-dihydro-5H-dibenzo[a,d]cyclo-hepten-5-yl)piperazin-1-yl) butyric acid ethyl ester.

$^1$H-NMR (300 MHz, CDCl$_3$) δ 7.10 (m, 8H), 4.09 (q, 2H), 2.95 (m, 3H), 2.78 (m, 2H), 2.30 (m, 12H), 1.76 (m, 2H), 1.20 (t, 3H).

The ester from the above step (1.2 g, 3.0 mmol), sodium hydroxide (0.8 g, 20 mmol) and water (2 ml) were dissolved in ethanol (50 ml) and allowed to react at 50° C. for 3 h. After cooling to room temperature, water (150 ml) was added and the reaction mixture was adjusted to pH 2 with 1 N hydrochloric acid and extracted with dichloromethane (3 x 50 ml). The combined organic extracts were dried (MgSO$_4$) and concentrated in vacuo. The resulting oil was stripped with acetone (2×20 ml), washed with acetone (20 ml) and dried under vacuum for 24 h leaving the title compound (0.93 g, 77%) as an amorphous solid.

Calculated for C$_{23}$H$_{28}$N$_2$O$_2$, HCl: C, 68.80%; H, 7.33%; N, 6.89%; Found: C, 68.90%; H, 7.29%; N, 6.99%.

$^1$H-NMR (300 MHz, DMSO-d$_6$) δ 12.3 (s, 1H), 11.0 (s, 1H), 7.15 (m, 8H), 4.17 (s, 1H), 3.89 (m, 2H), 3.36 (d, 3H (+H$_2$O)), 2.9 (m, 4H), 2.74 (q, 2H), 2.50 (m, 5H (+DMSO)), 2.30 (t, 2H), 1.87 (m, 2H).

Example 4
5-(4-(10,11-Dihydro-5H-dibenzo[a,d]cyclohepten-5-yl)piperazin-1-yl)pentanoic acid hydrochloride

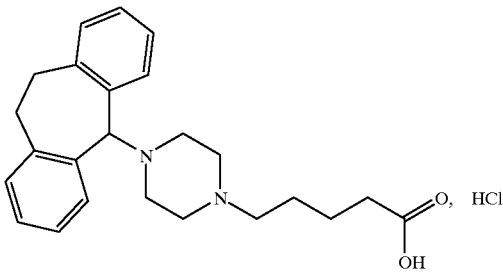

1-(10,11-Dihydro-5H-dibenzo[a,d]cyclohepten-5-yl)piperazine (1.0 g, 3.6 mmol), methyl 5-bromovalerate (0.80 g, 4.0 mmol), and potassium carbonate (0.5 g, 4 mmol) were suspended in acetonitrile (50 ml) and allowed to react at 50° C. for 4 h. The crude reaction mixture was subjected to column chromatography on silica gel (30 g) by first eluting with dichloromethane (50 ml) and then dichloromethane/methanol=9:1 (250 ml). This furnished 1.2 g (77%) of 5-(4-(10,11-dihydro-5H-dibenzo[a,d]cyclohepten-5-yl)-piperazin1-yl)-pentanoic acid methyl ester.

$^1$H-NMR (300 MHz, CDCl$_3$) δ 7.10 (m, 8H), 4.0 (m, 2H), 2.94 (s, 1H), 3.63 (s, 3H), 2.75 (m, 2H), 2.30 (m, 12H), 1.60 (m, 2H), 1.46 (m, 2H).

The ester from the above step (1.2 g, 3.0 mmol), sodium hydroxide (0.8 g, 20 mmol) and water (2 ml) was dissolved in ethanol (50 ml) and allowed to react at 50° C. for 3 h. After cooling to room temperature, water (150 ml) was added and the reaction mixture was adjusted to pH 2 with 1 N hydrochloric acid and extracted with dichloromethane (3×50 ml). The combined organic extracts were dried (MgSO$_4$) and concentrated in vacuo. The resulting oil was stripped with acetone (2×20 ml), washed with acetone (20 ml) and dried under vacuum for 24 h leaving the title compound (1.02 g, 80%) as an amorphous solid.

HPLC retention time=17.55 minutes (5 μm C18 4×250 mm column, eluting with a 20–80% gradient of 0.1% trifluoroacetic acid/acetonitrile and 0.1% trifluoroacetic acid/water over 30 minutes at room temperature)

$^1$H-NMR (300 MHz, DMSO-d$_6$) δ 12.1 (s, 1H), 10.8 (s, 1H), 7.10 (m, 8H), 4.16 (s, 1H), 3.87 (m, 2H), 3.32 (d, 3H), 2.95 (m, 4H), 2.73 (m, 2H), 2.59 (d, 2H), 2.40 (m, 3H) 2.24 (t, 2H), 1.75 (m, 2H), 1.46 (t, 2H).

Example 5
1-(3-(4-(6,11-Dihydrodibenzo[b,e]thiepin-11-ylidene)-1-piperidinyl)-1-propyl)-3-piperidinecarboxylic acid dihydrochloride

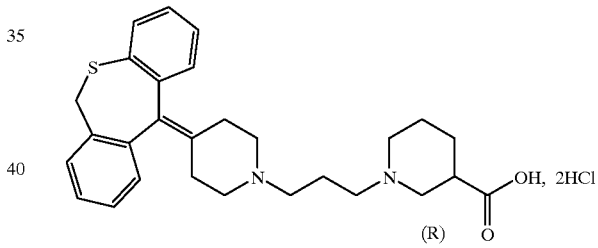

To a solution of 4-(6,11-dihydrodibenzo[b,e]thiepin-11-ylidene)piperidine (5,86 g, 20 mmol, prepared similarly as described in Ger.Offen 2 423 721) in 2-butanone (60 ml), potassium carbonate (4.2 g, 30 mmol) and 3-bromo-1-propyl tetrahydro-2-pyranyl ether (5.75 g, 25.8 mmol) were added and the reaction mixture was heated at reflux temperature for 20 h. After cooling to room temperature the mixture was filtered and the filtrate was evaporated. The residue was dissolved in a mixture of methanol (60 ml) and 5 N hydrochloric acid (20 ml). The solution was heated at reflux temperature for 15 minutes, methanol was distilled off and water (100 ml) followed by 5 N sodium hydroxide (40 ml) were added. The mixture was extracted with benzene, the organic extract was dried (K$_2$CO$_3$), filtered and the solvent was evaporated in vacuo. The residue was purified by column chromatography on silica gel (50 g) using ethyl acetate as eluent. This afforded 6.3 g (90%) of 4-(6,11-dihydrodibenzo[b,e]thiepin-11-ylidene)-1-piperidinepropanol as an oil.

TLC: R$_f$=0.35 (SiO$_2$: chloroform/ethanol/ammonium hydroxide=20:1:0.1)

The above alcohol (5.8 g, 16.5 mmol) was dissolved in benzene (60 ml), triethylamine (5 ml) and methanesulfonyl chloride (2.25 g, 19.6 mmol) were added and the reaction mixture was stirred for 5 h. After standing for 8 days, water (100 ml) was added and the phases were separated. The organic phase was dried (MgSO$_4$) and the solvent was evaporated in vacuo. The residue (2.25 g) was dissolved in 2-butanone (50 ml), and (R)-3-piperidinecarboxylic acid ethyl ester tartrate (1.6 g, 5.3 mmol) and potassium carbonate (3.0 g, 21.7 mmol) were added and the mixture was heated at reflux temperature for 20 h. After filtration the solvent was removed by evaporation in vacuo. The residue was purified by column chromatography on silica gel (40 g) using ethanol as eluent. This afforded 1.7 g (22%) of 1-(3-(4-(6,11-dihydrodibenzo[b,e]-thiepin-11-ylidene)-1-piperidinyl)-1-propyl)-3-piperidinecarboxylic acid ethyl ester as an oil.

TLC: R$_f$=0.22 (SiO$_2$: chloroform/ethanol/ammonium hydroxide=20:3:0.1)

The above ester (0.86 g, 1.8 mmol) was dissolved in ethanol (30 ml) and 5 N sodium hydroxide (2 ml) was added. The mixture was stirred at 40° C. for 24 h, ethanol was evaporated in vacuo and the residue was dissolved in water. Acetic acid (2 ml) was added and the mixture was extracted with dichloromethane (50 ml). After drying (MgSO$_4$), the solvent was evaporated in vacuo. The residue was triturated with diethyl ether affording 0.42 g (52%) of the title compound as an amorphous solid. The corresponding dihydrochloride was prepared by dissolving the base in acetone (5 ml) and treating the mixture with hydrogen chloride in diethyl ether. After dilution with ether (20 ml), filtration and drying, the dihydrochloride was obtained.

M.p. 245–255° C. (decomp.)

Calculated for C$_{28}$H$_{34}$N$_2$O$_2$S, 2 HCl, 0.25 H$_2$O: C, 62.79%; H, 6.78%: Cl, 13.24%; N, 5.23%; S, 5.99%; Found: C, 62.33%; H, 6.84%: Cl, 11.99%; N, 4.96%; S, 6.38%.

Example 6

(R)-1-(2-(4-(6,11-Dihydrodibenzo[b,e]thiepin-11-ylidene)piperidin-1-yl)ethyl)-3-piperidinecarboxylic acid dihydrochloride

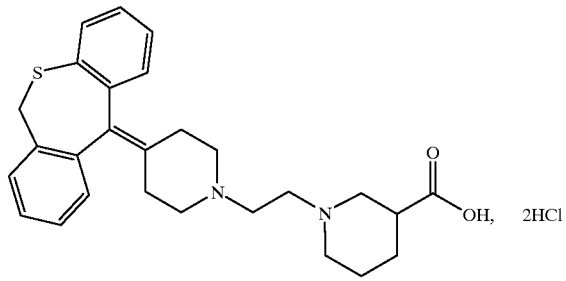

A mixture of 4-(6,11-dihydrodibenzo[b,e]thiepin-11-ylidene)piperidine hydrochloride (5.98 g, 18.1 mmol), 2-bromethanol (2.75 g, 22 mmol), potassium carbonate (6.0 g, 43.5 mmol) and acetone (100 ml) was stirred and heated at reflux temperature for 8 h. The mixture was filtered and the filtrate evaporated in vacuo. The residue was purified by column chromatography on silica gel (40 g) using a mixture of chloroform and ethanol (10:1) as eluent. This afforded 1.6 g (34%) of 4-(6.11-dihydrodibenzo[b,e]thiepin-11-ylidene)-1-piperidineethanol as an oil.

TLC: R$_f$=0.31 (SiO$_2$; chloroform/ethanol/ammonia= 20:1:0.05).

The above alcohol (1.6 g, 4.74 mmol) was dissolved in benzene (30 ml) and triethylamine (3 ml) was added. Methanesulfonyl chloride (0.8 g, 7 mmol) was added and the reaction mixture was stirred for 2 h. Water (50 ml) was added and the phases were separated. The organic phase was dried (MgSO$_4$) and the solvent evaporated in vacuo, affording a residue which was dissolved in N,N-dimethylformamide (10 ml). (R)-3-Piperidinecarboxylic acid ethyl ester tartrate (1.6 g, 5.2 mmol) and potassium carbonate (1.5 g, 10.8 mmol) were added and the mixture was heated at 100° C. for 11 h. Benzene (100 ml) and water (100 ml) were added and the phases were separated. The organic phase was dried (K$_2$CO$_3$) and the solvent evaporated in vacuo. The residue was purified by column chromatography on silica gel (20 g) using first ethyl acetate and then ethanol as eluents. This afforded 1.3 g (58%) of (R)-1-(2-(4-(6,11-dihydrodibenzo[b,e]thiepin-11-ylidene)piperidin-1-yl)ethyl)-3-piperidinecarboxylic acid ethyl ester as an oil.

TLC: R$_f$=0.20 (SiO$_2$; chloroform/ethanol/ammonia= 20:3;0.05).

The above ester (1.3 g, 2.7 mmol) was dissolved in ethanol (20 ml) and 5 N sodium hydroxide (2 ml) was added. The mixture was stirred at room temperature for 72 h, ethanol was evaporated in vacuo and water (40 ml) was added. The mixture was extracted with diethyl ether (40 ml) and the phases were separated. Acetic acid (2 ml) was added to the water phase and the mixture was extracted with dichloromethane (50 ml). The organic phase was dried (MgSO$_4$) and the solvent was evaporated in vacuo. The residue was dissolved in acetone and neutralised with hydrogen chloride in diethyl ether The precipitate was filtered off and crystallised from a mixture of ethanol, acetone and diethyl ether to give 0.47 g (30%) of the title compound as a solid.

M.p. 127–130° C.

Calculated for C$_{27}$H$_{32}$N$_2$O$_2$S, 2 HCl, H$_2$O, 0.5 CH$_3$COCH$_3$: C, 60.20%; H, 6.91%; N, 4.93%; S, 5.64%; Found: C, 60.11%; H, 6.78%; N, 4.91%; S, 5.55%.

Example 7

3-(4-(6,11-Dihydrodibenzo[b,e]thiepin-11-ylidene)-1-piperidine)propionic acid hydrochloride

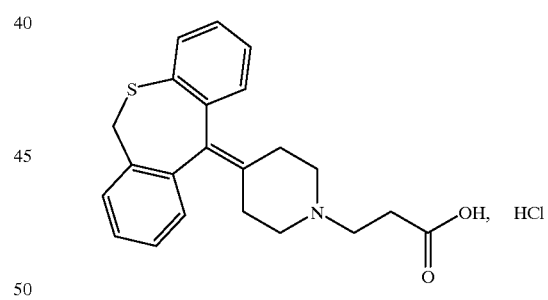

A mixture of 4-(6,11-dihydrodibenzo[b,e]thiepin-11-ylidene)piperidine (4.0 g, 0.0136 mol, prepared similarly as described in Ger.Offen 2 423 721) and ethyl acrylate (2.45 g, 0.0245 mol) in ethanol (50 ml) was heated at 70° C. for 2 h. The volatile materials were evaporated in vacuo and the residue (5.0 g) was dissolved in ethanol (25 ml) and neutralised with solution of oxalic acid in ethanol. Diethyl ether (30 ml) was added and the precipitated hydrogen oxalate was filtered off, washed with diethyl ether and crystallised from a mixture of ethanol and ether. After filtration and drying, this afforded 5.6 g (91%) of 3-(4-(6,11-dihydrodibenzo[b,e]thiepin-11-ylidene)-1-piperidine) propionic acid ethyl ester hydrogen oxalate.

A mixture of 3-(4-(6,11-dihydrodibenzo[b,e]thiepin-11-ylidene)-1-piperidine)propionic acid ethyl ester (liberated from the above hydrogen oxalate, 3.0 g, 0,0076 mol) was dissolved in ethanol (40 ml) and 4 N sodium hydroxide (10 ml) was added. The reaction mixture was stirred at room temperature for 10 h; then poured into dichloromethane (300 ml) and acidified with concentrated hydrochloric acid. The dichloromethane layer was separated, dried (MgSO$_4$) and evaporated in vacuo. The oily residue was re-evaporated twice with acetone and triturated with hot acetone to give 2.3 g (75%) of the title compound as an amorphous solid.

M.p. 176–186° C. (decomp.)

Calculated for $C_{22}H_{23}NO_2S$, HCl, 0.25 H$_2$O: C, 65.01%; H, 6.08%; Cl, 8.72%; N, 3,45%; S, 7.89%; Found: C, 65.13%; H, 6.13%; Cl, 8.62%; N, 3.46%: S. 7.92%.

Example 8

2-(4-(6,11-Dihydrodibenzo[b,e]thiepin-11-ylidene)-1-piperidinyl)acetic acid hydrochloride

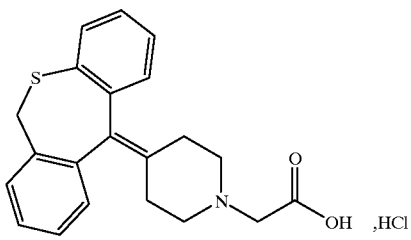

To a solution of 4-(6,11-dihydrodibenzo[b,e]thiepin-11-ylidene)piperidine (8.66 g, 0.0295 mol) in N,N-dimethylformamide (36 ml), ethyl bromoacetate (4.93 g, 0.0295 mol) and potassium carbonate (9.75 g, 0.0885 mol) were added and the reaction mixture was heated at 63–66° C. for 4.5 h. Water (250 ml) was added followed by benzene (150 ml). The phases were separated and the organic phase was washed with water (3×50 ml) and dried (MgSO$_4$). After evaporation in vacuo the residue was purified by column chromatography on silica gel (140 g) using benzene and a mixture of benzene and chloroform (1:1) as eluents. This afforded 3.26 g (29%) 2-(4-(6,11-dihydrodibenzo[b,e] thiepin-11-ylidene)-piperidin-1-yl)acetic acid ethyl ester as an oil.

TLC: R$_f$=0.48 (SiO$_2$: chloroform saturated with ammonia/ethanol=20:1)

To a solution of the above ester (3.26 g. 0.00859 mol) in ethanol (70 ml), 4 N sodium hydroxide (10 ml) was added and the reaction mixture was stirred at room temperature overnight. Concentrated hydrochloric acid (4.8 ml) and dichloromethane (480 ml) were added and the reaction mixture was shaken well. The phases were separated and the organic layer was dried (MgSO$_4$) and evaporated in vacuo. This was followed by re-dissolution and evaporation from acetone (2×100 ml). The residue was stirred with boiling acetone (300 ml), cooled and the precipitate was filtered to give 2.44 g (71.5%) of the title compound as a solid.

M.p.170–175° C.

Calculated for $C_{21}H_{21}NO_2S$, HCl, 0.5 H$_2$O: C, 63.54%; H, 5.84%; N, 3.53%; Cl, 8.93%; S, 8.08%; Found: C, 63.25%; H, 5.67%; N, 3.62%; Cl, 9.14%; S, 8.04%.

Example 9

4-(4-(6,11-Dihydrodibenzo[b,e]thiepin-11-ylidene)-1-piperidinyl)butyric acid acetate

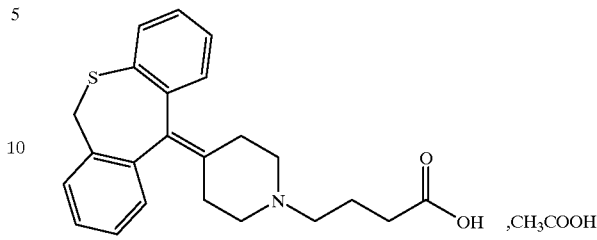

A mixture of 4-(6,11-dihydrodibenzo[b,e]thiepin-11-ylidene)piperidine hydrochloride (4.35 g, 13.2 mmol), 4-chlorobutyric acid ethyl ester (3.4 g, 24.2 mmol), potassium carbonate (4.0 g, 29 mmol), sodium iodide (1 g) and acetone (100 ml) was stirred and heated at reflux temperature for 14 h. The mixture was filtered and the filtrate evaporated in vacuo to give a residue which was purified by chromatography on silica gel (50 g) using chloroform as eluent. This afforded 2.85 g of 4-(4-(6,11-dihydrodibenzo [b,e]thiepin-11-ylidene)piperidine)-butyric acid ethyl ester as an oil.

TLC: R$_f$=0.55 (SiO$_2$: benzene/diethyl ether/ethanol= 10:10:2)

The above ester (2.85 g, 7 mmol) was dissolved in ethanol (50 ml) and 5 N sodium hydroxide (3 ml) was added. The mixture was stirred at room temperature for 20 h, ethanol was evaporated in vacuo and water (40 ml) was added. The mixture was extracted with diethyl ether (40 ml) and the phases were separated. Acetic acid (3 ml) was added to the aqueous phase and the mixture was extracted with dichloromethane (50 ml). The organic phase was dried (MgSO$_4$) and the solvent was evaporated in vacuo. The residue was triturated with diethyl ether and the precipitate was filtered off and dried to give 2.0 g (62%) of the title compound as an amorphous solid.

Calculated for $C_{23}H_{25}NO_2S$, CH$_3$COOH: C, 68.31%; H, 6.65%; N, 3.19%; S, 7.29%; Found: C, 68.36%; H, 6.77%; N. 3.12%; S, 7.39%.

Example 10

3-(4-(10,11-Dihydro-5H-dibenzo[a,d]cyclohepten-5-ylidene)-1-piperidine)propionic acid hydrochloride

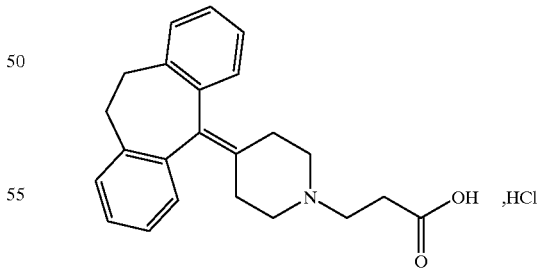

A mixture of 4-(10,11-dihydro-5H-dibenzo[a,d] cyclohepten-5-ylidene)piperidine (2.75 g, 0.01 mol) and ethyl acrylate (2.0 g, 0.02 mol) in ethanol (50 ml) was heated at 70° C. for 2 h. Volatile components were evaporated in vacuo, the residue (4.4 g) was dissolved in diethyl ether (50 ml) and the mixture was neutralised with a solution of oxalic acid (1.26 g) in ethanol (8 ml). The precipitated hydrogen oxalate was filtered off, washed with diethyl ether and crystallised from a mixture of ethanol and ether. After filtration and drying, this afforded 3.9 g (89%) of 3-(4-(10,11-dihydro-5H-dibenzo[a,d]cyclohepten-5-ylidene)-1-piperidine)propionic acid ethyl ester hydrogen oxalate.

3-(4-(10,11-Dihydro-5H-dibenzo[a,d]cyclohept-5-ylidene)-1-piperidine)propionic acid ethyl ester (liberated from the above hydrogen oxalate, 3.1 g, 0.00826 mol) was dissolved in ethanol (20 ml) and 4 N sodium hydroxide (6 ml) was added. The reaction mixture was stirred at room temperature for 10 h, then poured into dichloromethane (300 ml) and acidified with concentrated hydrochloric acid to pH=1. The dichloromethane layer was separated, dried (MgSO$_4$) and evaporated in vacuo. The oily residue was re-evaporated twice with acetone and then triturated with hot acetone. This afforded 2.55 g (80%) of the title compound as a solid.

M.p. 203–205° C.

Calculated for $C_{23}H_{25}NO_2$, HCl: C, 71.96%; H, 6.83%; Cl, 9.23%; N, 3.65%; Found: C, 71.57%; H, 7.00%; Cl, 9.01%; N, 3.73%.

What is claimed is:

1. A compound of formula I

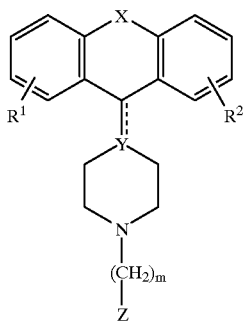

(I)

wherein $R^1$ and $R^2$ independently are hydrogen, halogen, trifluoromethyl, hydroxy, $C_{1-6}$-alkyl or $C_{1-6}$-alkoxy;

X is ortho-phenylene, —O—, —S—, —C(R$^6$R$^7$)—, —CH$_2$CH$_2$-, —CH=CH—CH$_2$—, —CH$_2$—CH=CH—, —CH$_2$—(C=O)—, —(C=O)—CH$_2$—, —CH$_2$CH$_2$CH$_2$—, —CH=CH—, —N(R$^8$)—(C=O)—, —(C=O)—N(R$^8$)—, —O—CH$_2$—, —CH$_2$—O—, —OCH$_2$O—, —S—CH$_2$—, —CH$_2$—S—, —(CH$_2$)N(R$^8$)—, —N(R$^8$)(CH$_2$)—, —N(CH$_3$)SO$_2$—, —SO$_2$N(CH$_3$)—, —CH(R$^{10}$)CH$_2$—, —CH$_2$CH(R$^{10}$)—, —(C=O)—, —N(R$^9$)— or —(S=O)— wherein R$^6$, R$^7$, R$^8$ and R$^9$ independently are hydrogen or C$_{1-6}$-alkyl, and wherein R$^{10}$ is C$_{1-6}$-alkyl or phenyl;

Y is N;

⋯ is optionally a single bond or a double bond, and ⋯ is a single bond when Y is N;

m is 2, 3, 4, 5 or 6; and

Z is —COOR$^3$ wherein R$^3$ is H or C$_{1-6}$-alkyl; or a pharmaceutically acceptable salt thereof.

2. A compound of claim 1 wherein R$^1$ and R$^2$ are selected from hydrogen, halogen, trifluoromethyl or C$_{1-6}$-alkyl.

3. A compound of claim 1 wherein m is 2, 3 or 4.

4. A compound of claim 1 wherein X is selected from —S—, —CH$_2$CH$_2$—, —CH=CH—, —O—CH$_2$—, —CH$_2$—O—, —OCH$_2$O—, —S—CH$_2$— or —CH$_2$—S—.

5. A compound of claim 1 wherein X is —CH$_2$CH$_2$—.

6. A compound of claim 1 wherein Z is —COOH.

7. A compound of claim 1 wherein X is —S—CH$_2$— or —CH$_2$—S—.

8. A compound selected from the group consisting of:

3-(4-(10,11-Dihydro-5h-dibenzo[a,d]cyclohepten-5-yl)piperazin-1-yl)propionic acid, 4-(4-(10,11-Dihydro-5H-dibenzo[a,d]cyclohepten-5-yl)piperazin-1-yl)butyric acid, and 5-(4-(10,11-Dihydro-5H-dibenzo[a,d]cyclohepten-5-yl)piperazin-1-yl)pentanoic acid, or a pharmaceutically acceptable salt thereof.

9. A method of preparing a compound of formula I, comprising:

a) reacting a compound of formula II

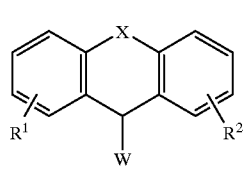

(II)

wherein W is a suitable leaving group, with a compound of formula III

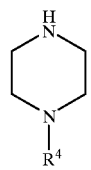

(III)

wherein R$^4$ is hydrogen, a suitable N-protecting group, —(CH$_2$)$_m$—CO$_2$R$^3$ or

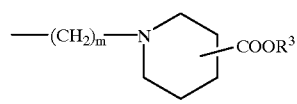

to form a compound of formula I, or b) reacting a compound of formula IV

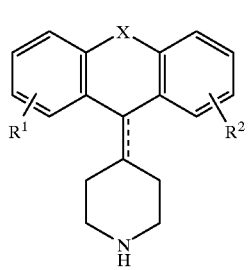

(IV)

with a compound of formula V

(V)

wherein Hal is a halogen, Z is —COOR³ or

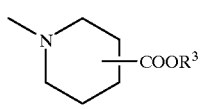

to form a compound of formula I.

10. A method of preparing a compound of formula Ia, comprising:

a) reacting a compound of formula II

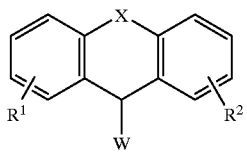
(II)

wherein W is a suitable leaving group, with a compound of formula III

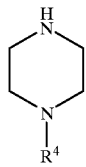
(III)

wherein R⁴ is hydrogen, a suitable N-protecting group or —(CH₂)$_m$—COOR³ to form a compound of formula Ia, or b) reacting a compound of formula IV

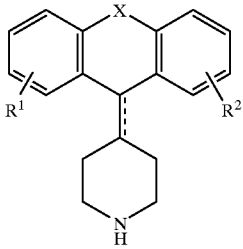
(IV)

with a compound of formula V

Hal(CH₂)$_m$—CO₂R³ (V)

wherein Hal means a halogen to form a compound of formula Ia.

11. A pharmaceutical composition comprising a therapeutically effective amount of a compound of claim 1 together with a pharmaceutically acceptable carrier or diluent.

12. The pharmaceutical composition of claim 11 comprising between 0.5 mg and 1000 mg of the compound per unit dose.

13. A method of treating insulin resistance comprising administering to a subject in need thereof an effective amount of a compound of claim 1.

14. A method of treating insulin resistance comprising administering to a subject in need thereof a pharmaceutical composition of claim 11.

15. A method of treating neurogenic inflammation comprising administering to a subject in need thereof a therapeutically effective amount of a compound of claim 1.

16. A method of treating neurogenic inflammation comprising administering to a subject in need thereof a pharmaceutical composition of claim 11.

17. A method of treating neurogenic inflammation associated with neuropathy or rheumatoid arthritis comprising administering to a subject in need thereof a therapeutically effective amount of a compound of claim 1.

18. A method of treating neurogenic inflammation associated with neuropathy or rheumatoid arthritis comprising administering to a subject in need thereof a pharmaceutical composition of claim 11.

* * * * *